United States Patent [19]

Ogata et al.

[11] Patent Number: 5,189,223
[45] Date of Patent: Feb. 23, 1993

[54] PROCESS FOR PREPARATION OF 4,4'-DIHYDROXYDIPHENYLSULFONE

[75] Inventors: Eiji Ogata, Wakayama; Nobuyuki Nate, Kainan, both of Japan

[73] Assignee: Konishi Chemical Ind. Co., Ltd., Wakayama, Japan

[21] Appl. No.: 678,332

[22] PCT Filed: Sep. 14, 1990

[86] PCT No.: PCT/JP90/01179
§ 371 Date: May 1, 1991
§ 102(e) Date: May 1, 1991

[87] PCT Pub. No.: WO91/04245
PCT Pub. Date: Apr. 4, 1991

[30] Foreign Application Priority Data

Sep. 14, 1989 [JP] Japan .............................. 1-239523
Dec. 29, 1989 [JP] Japan .............................. 1-340699
Dec. 29, 1989 [JP] Japan .............................. 1-340700

[51] Int. Cl.$^5$ .................. C07C 317/14; C07C 317/22
[52] U.S. Cl. ........................................ 568/33; 568/34
[58] Field of Search .................... 568/33, 34

[56] References Cited

U.S. PATENT DOCUMENTS

| 2,392,137 | 1/1946 | Foster | 568/33 |
| 2,833,828 | 5/1958 | Sauls | 568/33 |
| 3,065,274 | 11/1962 | Vegler et al. | 568/33 |
| 4,162,270 | 7/1979 | Ogata et al. | 568/33 |
| 4,382,147 | 5/1983 | Kitamura et al. | 568/33 |
| 4,820,831 | 4/1989 | Ogata et al. | 568/33 |
| 4,996,367 | 2/1991 | Ernst et al. | 568/33 |
| 5,041,677 | 8/1991 | Cooker et al. | 568/33 |
| 5,059,715 | 10/1991 | Stumpp et al. | 568/33 |
| 5,072,049 | 12/1991 | Stumpp et al. | 568/33 |

FOREIGN PATENT DOCUMENTS

| 0293037 | 11/1988 | European Pat. Off. |
| 0220004 | 11/1990 | European Pat. Off. |
| 1098239 | 8/1976 | Japan | 568/33 |
| 0243060 | 10/1986 | Japan | 568/33 |
| 86-06370 | 11/1986 | Japan | 568/33 |
| 2030566 | 4/1980 | United Kingdom |

OTHER PUBLICATIONS

Chemical Abstract; Japanese Examined Patent Publication No. 43936/1972.
Chemical Abstract; Japanese Unexamined Publication No. 24559/1986.
Chemical Abstract; Japanese Unexamined Publication No. 282358/1990.
Chemcial Abstract; Japanese Unexamined Publication No. 235857/1990.
J. Chem. Soc. 2854–6 (1949).

Primary Examiner—Marianne M. Cintins
Assistant Examiner—Margaret Page
Attorney, Agent, or Firm—Armstrong, Westerman, Hattori, McLeland & Naughton

[57] ABSTRACT

The present invention provides a process for preparing 4,4'-dihydroxydiphenylsulfone which comprises subjecting a phenol and a sulfonating agent to dehydration reaction in the presence of mesitylene as a reaction medium while the produced 4,4'-dihydroxydiphenylsulfone is suspended in the mesitylene, and a process for preparing 4,4'-dihydroxydiphenylsulfone, characterized in that after the foregoing dehydration reaction, the 4,4'-dihydroxydiphenysulfone obtained as suspended in the mesitylene and/or retained in a liquid-free solid form is subjected to reaction for isomerization of 2,4'-dihydroxydiphenylsulfone produced as a by-product into 4,4'-dihydroxydiphenylsulfone with heating at a temperature of not lower than that for isomerization of 2,4'-dihydroxydiphenylsulfone into 4,4'-dihydroxydiphenylsulfone.

11 Claims, No Drawings

PROCESS FOR PREPARATION OF 4,4'-DIHYDROXYDIPHENYLSULFONE

FIELD OF THE INVENTION

The present invention relates to a process for preparing 4,4'-dihydroxydiphenylsulfone (hereinafter referred to as "4,4'-DDS").

BACKGROUND ART

In recent years, a demand for 4,4'-DDS has been increased in the chemical industry, e.g. fields of fibers, resins or the like. Furthermore a demand for an extremely high-purity 4,4'-DDS has arisen to improve the quality of products in each field. Currently desired is the production of high-purity 4,4'-DDS in high yields as well as the provision of large-size manufacturing apparatus.

A process for preparation of 4,4'-DDS is known in which a phenol and a sulfonating agent are subjected to dehydration reaction in the presence of a solvent such as dichlorobenzene which is capable of dissolving the foregoing materials and the produced 4,4'-DDS. However, when the dehydration reaction is conducted in a solvent as in said process, the desired 4,4'-DDS as dissolved in the reaction product has an isomerization equilibrium with an isomer, i.e. 2,4'-dihydroxydiphenylsulfone (hereinafter referred to as "2,4'-DDS") produced as a by-product so that the obtained crude product contains 20 to 30% by weight of 2,4'-DDS as the impurity which decreases the purity and the yield of 4,4'-DDS. Further, it has been recently recognized that trihydroxytriphenyldisulfone (hereinafter referred to as "tri-compound") is produced as a by-product along with 2,4'-DDS.

In view of the above problems, the present inventors proposed a process for preparing a high-purity 4,4'-DDS in a high yield in which a phenol and a sulfuric acid undergo dehydration reaction in the presence of a solvent, and the 2,4'-DDS produced as a by-product is isomerized into 4,4'-DDS while gradually removing the solvent from the reaction mixture (Japanese Examined Patent Publication No.55-8972). The proposed process is intended to increase the purity and the yield of 4,4'-DDS in the following manner. In the process, only the 4,4'-DDS is precipitated from the reaction system by gradually removing the solvent utilizing the difference between 4,4'-DDS and 2,2'-DDS in the solubility in the solvent, whereby the isomerization equilibrium is shifted in the solution to induce the isomerization of 2,4'-DDS into 4,4'-DDS. However, the process causes the solidification of the reaction product solution on removal of the solvent into a viscous solid having no fluidity, and thus necessitates a special type of stirrer of high mechanical strength in the manufacture, resulting in difficulty in provision of a large-size manufacturing apparatus for mass production.

The present inventors also proposed processes involving the use of an aromatic sulfonic acid as a catalyst for the dehydration reaction or for the dehydration and isomerization reactions (Japanese Unexamined Patent Publications Nos.61-243059 and 61-243060). The proposed processes not only can reduce the time for the dehydration reaction and/or the isomerization reaction, but can prevent the production of 2,4'-DDS as a by-product in the dehydration reaction and the production of a tri-compound as a by-product in the dehydration and isomerization reactions. Yet the processes need to more markedly prevent the production of by-products and to further shorten the reaction time. Moreover, even the processes can not overcome the difficulty in handling the viscous product in the isomerization reaction.

Recently proposed is a process in which while a phenol and a sulfuric acid are subjected to dehydration reaction with heating in the presence of an aliphatic hydrocarbon-type suspending agent and an azeotropic agent, the 2,4'-DDS produced in the reaction is isomerized into 4,4'-DDS (Japanese Unexamined Patent Publication No.64-9970). The process, however, tends to be slow in the progress of dehydration reaction, and exhibits this tendency pronouncedly in the latter period of the reaction, consequently involving a prolonged period of reaction. Furthermore the process entails difficulties in completing the reaction even after a prolonged period of time, and insufficiently increasing the yield of 4,4'-DDS based on the sulfuric acid used. The above publication confusingly describes the purity and the yield of 4,4'-DDS and does not disclose the amount of obtained 4,4'-DDS. The yield of 4,4'-DDS based on the sulfuric acid used is not correctly set forth. The present inventors actually traced Example 3 of the publication showing the best result accomplished and found the following. Although the dehydration reaction in Example 3 smoothly proceeded in the initial stage of reaction, the amount of by-product water distilled off from the reaction system was reduced with the progress of reaction and extremely decreased one hour after the elevation of the temperature to 170° C., and the reaction was terminated in 2 hours. The distilled phenol was returned to the reaction system to sustain the progress of reaction, and an azeotropic agent was added several times for the progress of reaction. Nevertheless the progress of reaction remained so eminently slow that even after 16 hours 20 minutes of reaction, 4,4'-DDS was produced in a yield of only about 80% based on the sulfuric acid used, and thereafter no reaction continued. Since the reaction system tends to cause coagulation and sedimentation, a stirrer of high mechanical strength is needed to prevent such occurrences. An aliphatic hydrocarbon-type suspending agent has a high boiling point and thus an azeotropic agent must be conjointly used to conduct the dehydration reaction while removing the water from the reaction system. However, since the conjoint use of azeotropic agent represents a reaction medium of multicomponent composition, complicated controls and operations are unavoidably involved for the reaction and for recovery of components. The obtained reaction product has a blackish brown color which is difficult to remove by the purification procedure. Therefore only reaction products of low commercial value are obtainable.

DISCLOSURE OF THE INVENTION

An object of the present invention is to provide a process for preparing 4,4'-DDS, the process being capable of rapidly and easily conducting the dehydration reaction of a phenol and a sulfonating agent, and being capable of producing 4,4'-DDS within a short time in a high yield.

Another object of the invention is to provide a process for preparing 4,4'-DDS, the process being capable of easily performing the dehydration reaction of a phenol and a sulfonating agent and the reaction for the isomerization of the produced 2,4'-DDS into 4,4'-DDS using a conventional stirrer.

A further object of the invention is to provide a process for preparing 4,4'-DDS, the process being capable of significantly preventing the production of a tri-compound as a by-product in the dehydration reaction and/or the isomerization reaction, and being capable of producing 4,4'-DDS in a high yield.

According to the present invention, there is provided a process for preparing 4,4'-DDS which comprises subjecting a phenol and a sulfonating agent to dehydration reaction in the presence of mesitylene as a reaction medium while the produced 4,4'-DDS is suspended in the mesitylene. The present invention also provides a process for preparing 4,4'-DDS, characterized in that after the foregoing dehydration reaction, the 4,4'-DDS-containing suspension in the mesitylene and/or 4,4'-DDS-containing solids are subjected to reaction for isomerization of 2,4'-DDS produced as a by-product into 4,4'-DDS with heating at a temperature of not lower than that for isomerization of 2,4'-DDS into 4,4'-DDS.

The inventors' research found the following. When the dehydration reaction is performed in mesitylene while the produced 4,4'-DDS, i.e. the reaction product obtained by the dehydration reaction of phenol and sulfonating agent, is suspended in the mesitylene which is substantially incapable of dissolving the 4,4'-DDS, the reaction proceeds at a pronouncedly high rate and is completed at a relatively low temperature of 120° to 165° C. in a short time, a few hours, giving 4,4'-DDS in a satisfactorily high yield. The suspended state of the reaction system can be stably retained using a conventional stirrer without use of a stirrer of high mechanical strength. Further, since the mesitylene is the sole substance used as the reaction medium, the process allows the smooth progress of reaction and recovery of the medium without resort to special control. The obtained 4,4'-DDS has a pink color or pale brown color which can be readily eliminated by the purification procedure. The inventors' research further revealed the following. When the 4,4'-DDS obtained in the foregoing dehydration reaction in the form of a liquid phase with the solids as suspended in mesitylene or in the form of a solid phase formed by the removal of the liquid from the suspension is heated for isomerization of 2,4'-DDS produced as a by-product into 4,4'-DDS at a temperature of not lower than the isomerization temperature, the isomerization of the liquid phase can be performed by a conventional stirrer without causing coagulation or sedimentation, or that of the solid phase can be effected while it remains to be a crystal powder of very low consistency, thus without use of a special stirrer. Consequently the process enables the production of high-purity 4,4'-DDS in a high yield by means of a simple procedure and the mass production of 4,4'-DDS with ease on industrial basis.

Sulfonating agents useful in the invention include a wide range of conventional ones which are capable of introducing sulfonyl group into a phenol, such as concentrated sulfuric acid, sulfuric anhydride, fuming sulfuric acid, chlorosulfonic acid, phenolsulfonic acid, etc. among which concentrated sulfuric acid is preferred.

When, for example, a sulfuric acid is used as a sulfonating agent, the dehydration reaction proceeds as follows. A phenol is reacted with the sulfuric acid to give a phenolsulfonic acid as the reaction intermediate, which is reacted with the phenol to produce a dihydroxydiphenylsulfone. The reaction proceeds while producing water as a by-product. When a phenolsulfonic acid which is the reaction intermediate formed by use of sulfuric acid is used as a sulfonating agent, a dihydroxydiphenylsulfone is produced by the latter reaction alone.

The ratio of phenol and sulfonating agent used in the invention is not specifically limited. Yet when the amount of the former used is too small compared with that of the latter, the yield is decreased. An excessive amount of the former used increases the content of 2,4'-DDS due to the solubility of 4,4'-DDS in phenol. Hence an excessive amount of each component is undesirable. Usually these components are most preferably used in a stoichiometric amount or similar one. For example, when 2 moles of a phenol is reacted with 1 mole of a sulfonating agent such as sulfuric acid, chlorosulfonic acid or the like, about 1.9 to about 2.5 moles, preferably about 1.95 to about 2.3 moles, of a phenol is used per mole of a sulfonating agent. In the reaction of phenolsulfonic acid or like sulfonating agent with a phenol in an equimolar ratio, about 0.9 to about 1.5 moles, preferably about 0.95 to about 1.3 moles, of a phenol is used per mole of a phenolsulfonic acid.

It is essential in the present invention that a phenol and a sulfonating agent be subjected to dehydration reaction in the presence of mesitylene used as a reaction medium in such manner that the reaction proceeds while the 4,4'-DDS produced becomes suspended in the mesitylene.

Mesitylene (1,3,5-trimethylbenzene) has a boiling point of 165° C., and is capable of dissolving the starting materials under the reacting conditions of the invention but substantially incapable of dissolving the 4,4'-DDS produced. The amount of mesitylene used is not specifically limited insofar as the resulting suspension has sufficient fluidity to permit the agitation of the reaction system. In other words, an excess amount of mesitylene may be used as far as the amount is sufficient to maintain the suspended state of 4,4'-DDS produced in the reaction system until the completion of the dehydration reaction. In view of economy, a suitable amount of mesitylene is about 0.3 to about 5 times, preferably about 0.5 to about 2 times, the amount by weight of a phenol.

The dehydration reaction in the invention is easily conducted in a conventional manner. Usually the reaction is performed by subjecting the water produced as a by-product and the mesitylene with stirring to an azeotropic distillation for the separation and removal of the water, followed by refluxing the mesitylene. The dehydration reaction proceeds usually at a temperature of not lower than about 120° C. The temperature of the reaction system is elevated from 140° C. to approximately the boiling point (165° C.) of mesitylene with the progress of the reaction. An azeotropic agent need not be used because the water can be removed from the reaction system by the azeotropy of mesitylene and the water formed as a by-product. Since the mesitylene is the sole substance used as the reaction medium, the reacting operation and the recovery operation can be easily done. The suspended state of the reaction system can be maintained free of coagulation and sedimentation using a conventional stirrer, namely without use of specific stirrer. The completion of the reaction is simply detected by the termination of production of water as a by-product. According to the invention, the dehydration reaction proceeds at an eminently high rate and is completed only in a few hours, usually about 3 to about 6 hours. With the progress of the dehydration reaction, 2,4'-DDS is formed as a by-product and is isomerized into 4,4'-DDS when the temperature of the reaction system is not lower than the isomerization temperature. After accomplishing a certain degree of progress, the dehydration reaction and the isomerization reaction concurrently proceed. On completion of the dehydration reaction, a reaction product can be obtained in the form of a slurry in which at least about 94% by weight of 4,4'-DDS, up to about 4% by weight of 2,4'-DDS and up to about 2% by weight of a tri-compound are suspended in mesitylene.

The thus obtained slurry of reaction mixture can be easily separated into a liquid and a solid by removing the liquid by distillation or, when required, by reducing the temperature to a level which permits easy handling, e.g. about 100° C., followed by decantation, filtration or the like. The obtained solid is a mixture of fine crystal particles having an extremely low consistency. Alternatively the reaction mixture is poured into a sodium hydroxide solution to obtain an aqueous solution of the reaction product dissolved as a sodium salt, and the solution is left to stand, whereby the solution is easily separated into an upper phase of the mesitylene and a lower phase of the aqueous solution. When required, the foregoing aqueous solution or the sodium salt solution obtained by pouring the mixture of fine crystal particles in a sodium hydroxide solution is salted out after filtration with activated charcoal to achieve decolorization, whereby only a monometallic salt of 4,4'-DDS is precipitated. The precipitate is separated and purified by acid treatment, giving a highly purified 4,4'-DDS (by the purification method, e.g. as disclosed in Japanese Unexamined Patent Publication No.64-50855). The mesitylene thus separated from the product, being colorless and transparent, can be reused as it is.

A further purified 4,4'-DDS can be produced in a higher yield when the 4,4'-DDS-containing suspension and/or liquid-free solids obtained by removing the liquid therefrom is heated to a temperature of not lower than the isomerization temperature to undergo isomerization reaction for conversion of 2,4'-DDS produced as a by-product into 4,4'-DDS. The isomerization reaction is conducted using the 4,4'-DDS-containing suspension in mesitylene or the 4,4'-DDS-containing solids afforded by the removal of mesitylene. The isomerization reaction in mesitylene can be easily performed with mere stirring using a conventional stirrer without coagulation or sedimentation. The liquid-free solids, i.e. a mixture of fine crystal particles with a very low consistency which is easy to stir, are allowed to react for isomerization using a conventional stirrer without use of any specific stirrer of high strength. The isomerization reaction is completed in a few hours, usually about 2 to about 5 hours. In this way, a highly purified 4,4'-DDS can be produced in a high yield in a short time, usually up to about 10 hours (including the dehydration reaction time).

After the dehydration reaction, the 4,4'-DDS-containing suspension is reacted for isomerization according to the invention, as it is or after partial separation of the liquid or while distilling off the liquid. In the third case, a drying procedure can be omitted by synchronizing the completion of distillation of the whole liquid with the completion of isomerization reaction.

The method of removing the liquid is not specifically limited and includes conventional methods such as methods involving the vaporization of liquid at atmospheric or reduced pressure, filtration methods, etc.

The isomerization reaction of 4,4'-DDS-containing suspension is conducted with stirring at atmospheric or reduced pressure usually in the same reactor as used previously in the dehydration reaction. Optionally the reaction may be performed in another reactor. The reaction temperature is not lower than about 120° C., preferably about 140° to about 165° C. The stirring even if concurrently with the distillation of liquid is easily accomplished so that the solids can be kept well suspended in the reaction system.

In the isomerization reaction of 4,4'-DDS-containing solids according to the invention, the reaction mixture obtained by the dehydration reaction is separated into a liquid and a solid as by a filtration method, decantation method, instantaneous drying method or the like, followed by heating the resulting solids. When the 4,4'-DDS-containing suspension is reacted for isomerization while proceeding concurrently with distilling off substantially the whole liquid before completion of the reaction as described above, the obtained solids may be subsequently heated to complete the isomerization reaction.

The thus obtained solid for isomerization is a mixture of fine crystal particles having an extremely low consistency which have adsorbed thereon the phenolsulfonic acid usually produced as a reaction intermediate in the dehydration reaction or used as a sulfonating agent. Such phenolsulfonic acid acts well as an acid catalyst for accelerating the isomerization reaction.

When the isomerization reaction in the invention is effected at reduced pressure and the reaction product thus obtained is withdrawn as a solid at atmospheric pressure, an inert gas such as nitrogen or the like is preferably used to prevent the air oxidation of reaction product.

The isomerization reaction of 4,4'-DDS-containing solids is performed in a closed or opened container with heating at a temperature of about 120° to about 200° C., preferably about 140° to about 180° C., at atmospheric or reduced pressure with stirring when so required. The isomerization reaction with stirring can be easily performed using a conventional powder-handling apparatus, such as a vacuum dryer or the like. While the isomerization reaction in the invention may be carried out in the atmosphere, it is preferably conducted in the atmosphere of nitrogen or like inert gas.

The thus obtained reaction product is a liquid-free mixture of fine crystal particles which contains about 96% by weight or more of 4,4'-DDS on completion of isomerization reaction of 4,4'-DDS-containing suspension, about 97% by weight or more thereof on completion of isomerization reaction of the solid product. Namely 4,4'-DDS is produced in a yield of at least about 95%. When required, the obtained mixture of fine crystal particles is easily purified into a purified 4,4'-DDS by the method disclosed, e.g. in above-cited Japanese Unexamined Patent Publication No.64-50855.

The present inventors' research also revealed the following. When the dehydration reaction or the dehydration and isomerization reaction according to the invention are effected in the presence of an aromatic polysulfonic acid represented by the formula (1)

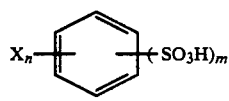

(1)

wherein X is a halogen atom, or an alkyl group having 1 or 2 carbon atoms, n is 0, 1 or 2 and m is 2 or 3, not only the production of 2,4'-DDS as a by-product in the dehydration reaction can be more notably prevented, but also surprisingly the production of tri-compound as a by-product in the dehydration reaction and/or isomerization reaction can be markedly reduced, i.e. substantially to zero. Consequently even the dehydration reaction alone gives 4,4'-DDS having a purity of about 97% by weight or more, in a yield of about 96% or more. The purity and the yield of 4,4'-DDS can be further increased by the isomerization reaction done subsequent to the dehydration reaction. Moreover, use of the foregoing catalyst can reduce the reaction temperature and can decrease the reaction time.

Aromatic polysulfonic acids of the formula (1) useful in the invention include a wide range of those heretofore used which do not participate in the foregoing dehydration reaction and which are stable in the reaction system. Examples of such aromatic polysulfonic acids are benzene-1,3-disulfonic acid, chlorobenzene-2,4-disulfonic acid, bromobenzene-2,4-disulfonic acid, fluorobenzene-2,4disulfonic acid, toluene-2,4-disulfonic acid, ethylbenzene-2,4-disulfonic acid, benzene-1,3,5-trisulfonic acid, chlorobenzene-2,4,6-trisulfonic acid, bromobenzene-2,4,6-trisulfonic acid, fluorobenzene-2,4,6-trisulfonic acid, toluene-2,4,6-trisulfonic acid, ethylbenzene-2,4,6trisulfonic acid, etc. among which benzene-1,3-disulfonic acid and benzene-1,3,5-trisulfonic acid are preferred. The above-exemplified aromatic polysulfonic acids can be used singly or at least two of them are usable in mixture. The amount of aromatic polysulfonic acid can be suitably selected from a wide range without specific limitation insofar as it is in the range of catalytic amount. A typical amount is about 0.5 to about 10 mole %, preferably about 2 to about 5 mole %, based on the sulfonating agent used. While an increased amount of aromatic polysulfonic acid used does not adversely affect the reaction, the amount of 10 mole % or less is preferred in view of economy. Useful aromatic polysulfonic acids include commercially available ones, crude products synthesized in a conventional manner from benzene, halogenated benzene or alkylbenzene and a sulfonating agent, and purified products thereof. The aromatic polysulfonic acid, which even in a small amount can achieve the desired effect, would pose substantially no economic problem if thrown away after the reaction. When required, the acid remaining after the separation of the desired product can be reused.

The aromatic polysulfonic acid may be added for use in the dehydration reaction alone or in the dehydration reaction and the isomerization reaction of 4,4'-DDS-containing suspension or solids. For use in the dehydration and isomerization reactions, the acid may be added in either the dehydration reaction or the subsequent isomerization reaction. Use of the aromatic polysulfonic acid can markedly prevent the production of tri-compound as a by-product.

The present invention will be described below in greater detail with reference to the following examples and comparison examples.

The composition of the products obtained in the examples and the comparison examples was confirmed by a high performance liquid chromatography.

EXAMPLE 1

A 100.0 g quantity of 98.1% sulfuric acid (1.00 mole of sulfuric acid) was added dropwise with stirring to a mixture of 188.2 g (2.00 moles) of phenol and 100 ml of mesitylene. The resulting mixture was heated with stirring using an oil bath. At about 145° C., the reaction mixture began to boil to initiate the distillation. The distillate was condensed by a condenser and separated into two phases by a trap. The upper organic phase was continuously returned to the reaction system. After about 5 hours of heating, the temperature of the reaction system reached 165° C., 38 ml of water was removed from the lower phase by the trap and both values remained constant. The product obtained at this stage had a composition (ratio by weight) of 4,4'-DDS: 2,4'-DDS:tri-compound=93.6:4.3:2.1. The total yield of the three components was 97.0% and the yield of 4,4'-DDS alone was 90.7%, based on the sulfuric acid used.

EXAMPLE 2

The same procedure as in Example 1 was repeated and the reaction system was maintained as it was at the same temperature for 5 hours. The obtained product had a composition (ratio by weight) of 4,4'-DDS:2,4'-DDS: tri-compound=95.4:2.6:2.0. The total yield of the three components was 97.5% and the yield of 4,4'-DDS alone was 93.0%, based on the sulfuric acid used.

EXAMPLE 3

The same procedure as in Example 1 was repeated and 30 ml of the liquid portions (mesitylene and unreacted phenol) in the reaction system were collected and removed. The remaining components were further maintained at 165° C. with stirring for 5 hours. The product obtained had a composition (ratio by weight) of 4,4'-DDS:2,4'-DDS: tri-compound=95.9:2.3:1.8. The total yield of the three components was 97.9% and the yield of 4,4'-DDS was 93.9%, based on the sulfuric acid used.

EXAMPLE 4

The same procedure as in Example 1 was repeated. Thereafter, substantially whole liquid portion in the reaction system was gradually collected over a period of 3 hours by maintaining the temperature of the oil bath at 165° C. and controlling the reduction of the pressure over the reaction system, whereupon the isomerization reaction was completed. The pressure was eventually reduced to 10 mm·Hg.

The product thus obtained had a composition (ratio by weight) of 4,4'-DDS:2,4'-DDS:tri-compound=96.9: 1.6:1.5. The total yield of the three components was 98.5% and the yield of 4,4'-DDS was 95.4%, based on the sulfuric acid used.

EXAMPLE 5

A 100.0 g quantity of 98.1% sulfuric acid (1.00 mole of sulfuric acid) was added dropwise with stirring to a mixture of 190.1 g (2.02 moles) of phenol and 190 ml of mesitylene. The resulting mixture was heated with stirring using an oil bath. At about 145° C., the reaction mixture began to boil to initiate the distillation. The distillate was condensed by a condenser and separated into two phases by a trap. The upper organic phase was continuously returned to the reaction system. After about 5 hours of heating, the temperature of the reaction system reached 165° C., 38 ml of water was removed from the lower phase by the trap and both values remained constant.

Thereafter, substantially whole liquid portion in the reaction system was collected over a period of 30 minutes by maintaining the temperature of the bath at 165° C. and controlling the reduction of pressure over the reaction system. The pressure was restored to normal pressure by introduction of nitrogen.

The obtained crystal powder was further heated at 165° C. for 3 hours to complete the isomerization reaction. The obtained product had a composition (ratio by weight) of 4,4'-DDS:2,4'-DDS:tri-compound=97.0:1.6:1.4. The total yield of the three components was 98.2% and the yield of 4,4'-DDS was 95.3%, based on the sulfuric acid used.

EXAMPLE 6

The same procedure as in Example 1 was repeated and the obtained slurry of reaction mixture was filtered at 100° C. for separation into solids and liquids. The obtained crystal powder was fed to the reactor in an oil bath maintained at 165° C. and the mesitylene and the like adhering to the powder were distilled off under reduced pressure for 15 minutes. The residue was heated in the hermetically sealed reactor under reduced pressure with stirring at the same temperature for 3 hours to stop the isomerization.

The product thus obtained had a composition (ratio by weight) of 4,4'-DDS:2,4'-DDS:tri-compound=97.0:1.6:1.4. The total yield of the three components was 98.2% and the yield of 4,4'-DDS was 95.3%, based on the sulfuric acid used.

EXAMPLE 7

A 100.0 g quantity (1.00 mole) of 98.1% sulfuric acid was added dropwise with stirring to a mixture of 197.6 g (2.10 moles) of phenol, 200 ml of mesitylene and 11.9 g (0.05 mole) of benzene-1,3-disulfonic acid. The resulting mixture was heated using an oil bath and the reaction mixture began to boil at about 145° C. to initiate the distillation. The distillate was condensed by a condenser and separated into two phases by a trap. The upper organic phase was continuously returned to the reaction system. After about 4 hours of distillation, the temperature of the reaction system reached 165° C., and 38 ml of water was removed from the lower phase by the trap. Both values remained constant. The product thus obtained had a composition (ratio by weight) of 4,4'-DDS:2,4'-DDS =97.9:2.1. The total yield of the two components was 99.2% and the yield of 4,4'-DDS was 97.1%, based on the sulfuric acid used.

EXAMPLE 8

The same procedure as in Example 7 was repeated with the exception of using 0.05 mole of benzene-1,3,5-trisulfonic acid (containing 20% of disulfonic acid) in place of 0.05 mole of benzene-1,3-disulfonic acid. The procedure gave a product having a composition (ratio by weight) of 4,4'-DDS:2,4'-DDS=97.5:2.5. The total yield of the two components was 99.3% and the yield of 4,4'-DDS was 96.8%, based on the sulfuric acid used.

EXAMPLE 9

A product was obtained in the same manner as in Example 7 with the exception of using 0.05 mole of chlorobenzene-2,4-disulfonic acid (containing 40% of monosulfonic acid) in place of 0.05 mole of benzene-1,3-disulfonic acid. The product thus obtained had a composition (ratio by weight) of 4,4'-DDS:2,4'-DDS: tri-compound=96.8:3.0:0.2. The total yield of the three components was 99.2% and the yield of 4,4'-DDS was 96.0%, based on the sulfuric acid used.

EXAMPLE 10

The same procedure as in Example 7 was repeated with the exception of using 0.05 mole of toluene-2,4-disulfonic acid in lieu of 0.05 mole of benzene-1,3-disulfonic acid. The procedure gave a product having a composition (ratio by weight) of 4,4'-DDS:2,4'-DDS:tri-compound=96.6:3.0:0.4. The total yield of the three components was 99.2% and the yield of 4,4'-DDS was 95.8%, based on the sulfuric acid used.

EXAMPLE 11

The same procedure as in Example 7 was repeated and 120 ml of the liquid portions in the reaction system were collected and removed. The residue was further maintained at 165° C. with stirring with refluxing for 3 hours. The product obtained had a composition (ratio by weight) of 4,4'-DDS:2,4'-DDS=98.1:1.9. The total yield of the two components was 99.3% and the yield of 4,4'-DDS was 97.4%, based on the sulfuric acid used.

EXAMPLE 12

The same procedure as in Example 7 was repeated. Thereafter, substantially whole liquid portion in the reaction system was collected over a period of 30 minutes by maintaining the temperature of the oil bath at 165° C. and controlling the reduction of pressure over the reaction system. The pressure was restored to normal pressure and the residue was maintained at an oil bath temperature of 165° C. for 3 hours, whereby the isomerization reaction was completed. The product thus obtained had a composition (ratio by weight) of 4,4'-DDS: 2,4'-DDS=98.8:1.2. The total yield of the two components was 99.5% and the yield of 4,4'-DDS was 98.3%, based on the sulfuric acid used.

COMPARISON EXAMPLE 1

A 100.0 g quantity of 98.1% sulfuric acid (1.00 mole of sulfuric acid) was added dropwise with stirring to a mixture of 190.1 g (2.02 moles) of phenol and 190 ml of orthodichlorobenzene and the resulting mixture was heated. At about 150° C., the reaction mixture began to boil to initiate the distillation. The distillate was condensed by a condenser and separated into two phases by a trap and the lower organic phase was continuously returned to the reaction system. After about 5 hours of heating, the temperature of the reaction system reached 179° C., 37 ml of water was removed from the upper phase by the trap and both values remained constant. The product obtained at this stage had a composition (ratio by weight) of 4,4'-DDS 2,4'-DDS:tri-compound=71.9:22.7:5.4. The total yield of the three components was 91.7% and the yield of 4,4'-DDS was 65.9%, based on the sulfuric acid used.

COMPARISON EXAMPLE 2

A 250 ml-vol. three-necked flask (in $N_2$ atmosphere) equipped with a thermometer, a dropping funnel, a mechanical stirrer, an oil bath, a sampling aperture and a Dean-Stark** trap was charged with 100.0 g of phenol (1.06 moles), 139 ml of ISOPAR H (trade name of an aliphatic saturated hydrocarbon) and 8.7 ml of ISOPAR E (trade name of an aliphatic saturated hydrocarbon) as an azeotropic agent.

A 52.1 g quantity of sulfuric acid (0.53 mole) was added dropwise at 100° C. over a period of 30 minutes.

The reaction mixture was heated to initiate the reaction. The distillate contained water, the azeotropic agent and a considerable quantity of phenol and was separated into three phases in the trap, the three phases consisting of, in descending order, the azeotropic agent phase, phenol-saturated aqueous phase and water-saturated phenol phase, because the phenol did not dissolve in the azeotropic agent. The amount of the distillate gradually decreased with the progress of the reaction, and extremely decreased 1 hour after the elevation of temperature to 170° C. Two hours after heating to 170° C., substantially no distillation occurred and the reaction terminated. The total amount of water produced as a by-product at this stage was 10 g and the conversion was found to be low.

In view of this, the phenol phase was returned to the reaction system in order to reduce the loss of a considerable quantity of phenol distilled off from the reaction system. Simultaneously the reaction was allowed to continue while maintaining composition of the reaction medium by adding the azeotropic agent to the reaction system several times.

The end product obtained 16 hours and 20 minutes after the initiation of the heating had a composition (ratio by weight) of 4,4'-DDS:2,4'-DDS: tri-compound=95.1:2.9:2.0. The yield of 4,4'-DDS was 80% based on the sulfuric acid used.

It was not possible to continue the reaction any longer.

We claim:

1. A process for preparing 4,4'-dihydroxydiphenylsulfone, comprising reacting a phenol and a sulfonating agent in the presence of mesitylene as a reaction medium at a temperature not lower than about 120° C., thereby producing a suspension containing 4,4'-dihydroxydiphenylsulfone in the mesitylene.

2. A process for preparing 4,4'-dihydroxydiphenylsulfone according to claim 1, wherein the suspension containing 4,4'-dihydroxydiphenylsulfone in the mesitylene is subjected to an isomerization reaction 2,4'-dihydroxydiphenylsulfone produced as a by-product into 4,4'-dihydroxydiphenylsulfone, by heating at a temperature not lower than about 120° C.

3. A process for preparing 4,4'-dihydroxydiphenylsulfone according to claim 2, wherein a portion of liquid components is removed from the suspension containing 4,4'-dihydroxydiphenylsulfone in the mesitylene prior to the isomerization reaction.

4. A process for preparing 4,4'-dihydroxydiphenylsulfone according to claim 2, wherein liquid components are distilled off during the isomerization reaction while retaining the 4,4'-dihydroxydiphenylsulfone suspended in the mesitylene.

5. A process for preparing 4,4'-dihydroxydiphenylsulfone according to claim 4, wherein substantially all the liquid components are distilled off.

6. A process for preparing 4,4'-dihydroxydiphenylsulfone according to claim 1, further comprising the steps of removing liquid components from the suspension to isolate a crystal powder mixture, and heating the crystal powder mixture to a temperature not lower than about 120° C. for isomerization of 2,4'-dihydroxydiphenylsulfone contained in the mixture into 4,4'-dihydroxydiphenylsulfone.

7. A process for preparing 4,4'-dihydroxydiphenylsulfone according to claim 6, wherein the suspension is obtained on completion of the reaction of the phenol and the sulfonating agent.

8. A process for preparing 4,4'-dihydroxydiphenylsulfone according to claim 6, wherein the suspension is obtained before completion of the isomerization reaction.

9. A process for preparing 4,4'-dihydroxydiphenylsulfone according to claim 1, wherein the reaction of the phenol and sulfonating agent is carried out in the presence of an aromatic polysulfonic acid represented by the formula

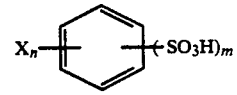

wherein X is a halogen atom, or an alkyl group having 1 or 2 carbon atoms, n is 0, 1 or 2 and m is 2 or 3.

10. A process for preparing 4,4'-dihydroxydiphenylsulfone according to claim 2, wherein the isomerization reaction is carried out in the presence of an aromatic polysulfonic acid represented by the formula

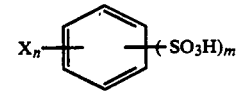

wherein X is a halogen atom, or an alkyl group having 1 or 2 carbon atoms, n is 0, 1 or 2 and m is 2 or 3.

11. A process according to claim 9 or 10, wherein the aromatic polysulfonic acid is one of benzene-1,3-disulfonic acid and benzene-1,3,5-trisulfonic acid.

* * * * *